US00PP11323P

United States Patent [19]

Boeder

[11] Patent Number: Plant 11,323

[45] Date of Patent: Apr. 4, 2000

[54] CHRYSANTHEMUM PLANT NAMED 'PARAKEET'

[75] Inventor: Mark Boeder, West Wittering, United Kingdom

[73] Assignee: Cleangro Limited, West Sussex, United Kingdom

[21] Appl. No.: 09/038,790

[22] Filed: Mar. 11, 1998

[51] Int. Cl.[7] ..... A01H 5/00

[52] U.S. Cl. ..... Plt./289

[58] Field of Search ..... Plt./289

[56] References Cited

U.S. PATENT DOCUMENTS

| | | | |
|---|---|---|---|
| P.P. 6,404 | 11/1988 | Mack et al. | Plt./289 |
| P.P. 6,621 | 2/1989 | Mack et al. | Plt./289 |
| P.P. 10,463 | 6/1998 | Wain | Plt./289 |

*Primary Examiner*—Howard J. Locker
*Attorney, Agent, or Firm*—Christie, Parker & Hale, LLP

[57] ABSTRACT

A new plant variety of Chrysanthemum producing yellow flowers.

1 Drawing Sheet

BACKGROUND OF THE INVENTION

The present invention is directed to a new and distinct variety of Chrysanthemum botanically classified as *Dendranthema grandiflora*. The varietal denomination of the new chrysanthemum is 'Parakeet'.

The female parent of the new variety is an unnamed, undistributed variety identified as 'G12-C1' and the male parent is a undistributed, unnamed, seedling identified as 'G23-C1'. The new variety has been asexually reproduced by vegetative cuttings in Ventura County, Calif. and the distinguishing characteristics are retained through successive generations of asexual reproduction.

SUMMARY OF THE INVENTION

'Parakeet' is a pot type Chrysanthemum plant variety that produces yellow flowers.

BRIEF DESCRIPTION OF ILLUSTRATION

The accompanying photograph shows a typical specimen of the new variety with colors being as nearly true as possible with illustrations of this type.

DESCRIPTION OF THE PLANT

The following description of the new variety is of specimens grown in a greenhouse in Ventura County, Calif. in the month of October. 'Parakeet' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once ten days after planting which results in about 3 breaks per pinch. It has been observed that the shelf life of 'Parakeet' is about 26 days with the response time of about 6.5 weeks. No treatment with growth retardant is required. Useful growing conditions include night temperatures of about 64°–66° F., day temperatures of about 80°–85° F. and about 5,000 foot-candles of light.

Plant:

*Habit.*—Upright.
*Height.*—About 30 cm.
*Number of breaks from pinch.*—About 3.

*Typical container sizes commercially grown in.*—4 inch, 6 inch, 1 gallon and 3 gallon containers.
*Length of lateral branches.*—About 19 cm.
*Stem color.*—Near 146C.

Foliage:

*Leaf arrangement.*—Alternate.
*Number of leaves per lateral branch.*—About 11.
*Leaf size.*—Length: About 6 cm. Width: About 4 cm.
*Leaf shape.*—Ovate.
*Attachment.*—Petioled.
*Leaf apex.*—Obtuse.
*Base.*—Tapered.
*Margin.*—Serrate, lobed.
*Aspect.*—Undulating.
*Surface.*—Top: Pubescent. Bottom: Lightly pubescent.
*Petiole.*—Length: About 1.3 cm. Color: Near 146C.
*Color.*—Mature leaf: Top: Near 147A. Bottom: Near 137B. Young leaf: Top: Near 137A. Bottom: Near 137D.

Flower:

*Inflorescence form.*—Cyme.
*Flower form.*—Decorative.
*Number of blooms per branch.*—About 7.
*Diameter of fully expanded bloom.*—About 4.5 cm.
*Depth of fully expanded bloom.*—About 2.5 cm.
*Sepal number*—About 35. Color: Near 138A.
*General appearance of sepals.*—Thin with highly membranous margins.
*Peduncle length.*—About 8.5 cm at lower most point on the flowering sterm, about 3 and 4 cm at upper most peduncle. Habit: Upright. Surface: Lightly pubescent. Strength: Very sturdy.
*Flower bud shape.*—Flattened shpere. Diameter: About 0.9 cm. Height: About 0.6 cm.
*Ray florets.*—Number per flower: About 250. Shape: Elliptic. Apex: About 4 lobed. Base: Tapered. Margin: Entire. Aspect: Recurved. Length: About 2.3 cm. Width: About 0.9 cm.
*Disc florets.*—Number per flower: About 5. Shape: Tubular. Length: About 0.4 cm. Width: About 0.1 cm.
*Fragrance.*—Faint.

Flower Color:

*General flower coloration.*—Bright yellow.
*Ray florets, top side.*—Immature: Near 7A. Mature: Near 9A. Fading: Near 12B.

*Ray floret, under side.*—Immature: Near 10B. Mature: Near 12C. Fading: Near 10C.

*Disc florets.*—Mature: Near 12C.

*Changes as the flower ages.*—Very little fading; flower becomes very round.

Reproductive organs:

*Ray florets.*—Pistillate. Stigma shape: 2 forked. Stigma color: Near 6A. Style length: About 0.5 cm.

*Disc florets.*—Stigma shape: linear. Stigma color: Near 3C. Style Length: About 0.2 cm. Stamen number: About 6. Anther length: About 0.1 cm. Pollen color: Near 12A. Pollen quantity: Moderate.

What is claimed is:

1. A new and distinct Chrysanthemum plant of the variety substantially as herein shown and described.

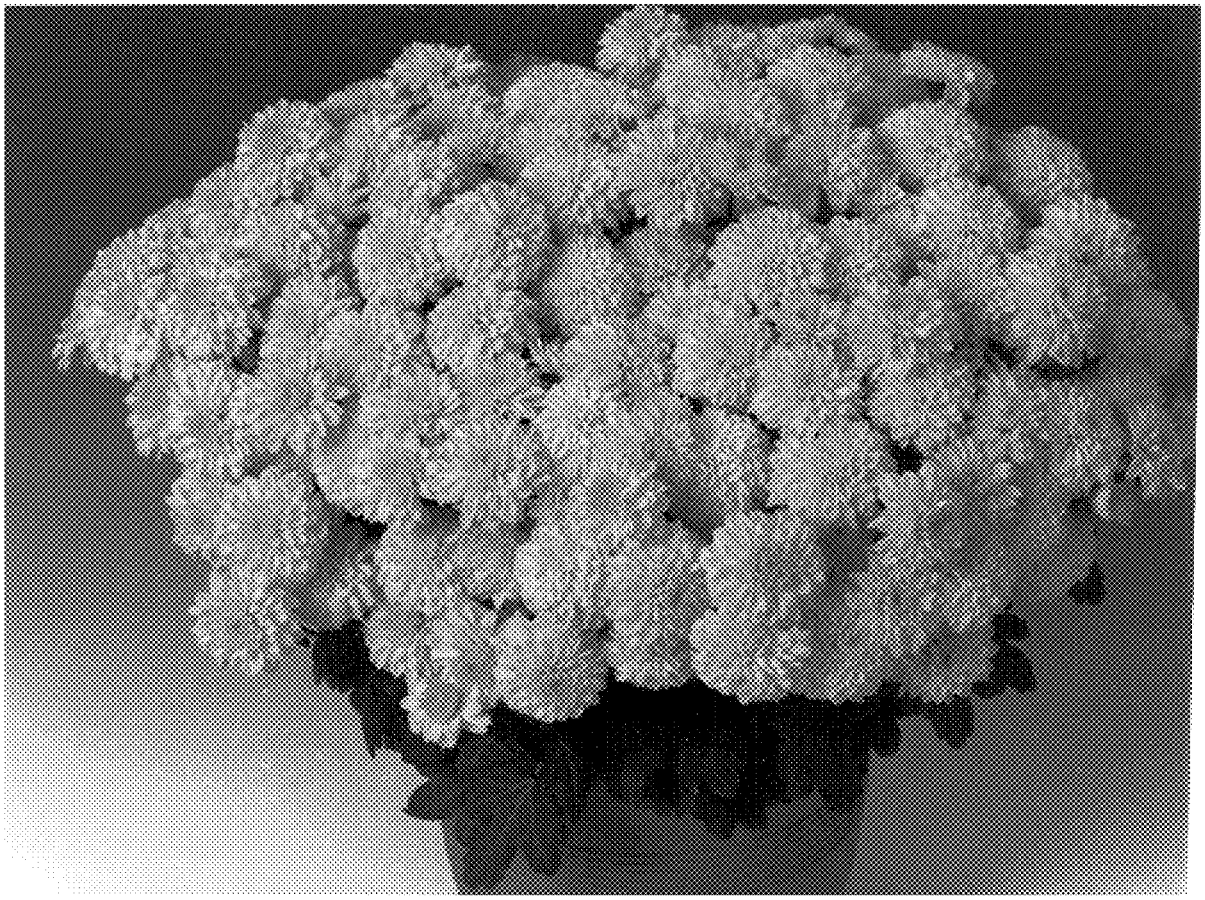

* * * * *